(12) United States Patent
Chappa (10) Patent No.: US 7,709,049 B2
(45) Date of Patent: May 4, 2010

(54) METHODS, DEVICES, AND COATINGS FOR CONTROLLED ACTIVE AGENT RELEASE

(75) Inventor: Ralph A. Chappa, Prior Lake, MN (US)

(73) Assignee: SurModics, Inc., Eden Prairie, MN (US)

( * ) Notice: Subject to any disclaimer, the term of this patent is extended or adjusted under 35 U.S.C. 154(b) by 1241 days.

(21) Appl. No.: 11/223,811

(22) Filed: Sep. 9, 2005

(65) Prior Publication Data

US 2006/0057277 A1 Mar. 16, 2006

Related U.S. Application Data

(60) Provisional application No. 60/608,638, filed on Sep. 10, 2004.

(51) Int. Cl.
*A61L 33/00* (2006.01)
*A41D 19/00* (2006.01)
*B05D 7/00* (2006.01)
*A61F 2/00* (2006.01)

(52) U.S. Cl. .............. 427/2.24; 427/2.25; 427/2.3; 427/427.4; 424/423; 424/426

(58) Field of Classification Search .......... 427/2.24, 427/2.25, 2.3, 427/4; 424/423, 426
See application file for complete search history.

(56) References Cited

U.S. PATENT DOCUMENTS

| | | | |
|---|---|---|---|
| 4,638,045 A | 1/1987 | Kohn et al. | |
| 6,042,875 A | 3/2000 | Ding et al. | |
| 6,214,901 B1 | 4/2001 | Chudzik et al. | |
| 6,254,921 B1 | 7/2001 | Chappa et al. | |
| 6,344,035 B1 | 2/2002 | Chudzik et al. | |
| 6,406,754 B2 | 6/2002 | Chappa et al. | |
| 6,562,136 B1 | 5/2003 | Chappa et al. | |
| 6,709,712 B2 | 3/2004 | Chappa et al. | |
| 6,872,225 B1 * | 3/2005 | Rowan et al. | 623/1.15 |
| 6,890,583 B2 | 5/2005 | Chudzik et al. | |
| 7,008,667 B2 * | 3/2006 | Chudzik et al. | 427/2.1 |
| 7,097,850 B2 * | 8/2006 | Chappa et al. | 424/423 |
| 2002/0065551 A1 * | 5/2002 | Koole et al. | 623/1.25 |
| 2002/0094440 A1 * | 7/2002 | Llanos et al. | 428/421 |

(Continued)

FOREIGN PATENT DOCUMENTS

WO  WO 9955396 A1 * 11/1999

(Continued)

*Primary Examiner*—Johann R Richter
*Assistant Examiner*—Abigail Fisher
(74) *Attorney, Agent, or Firm*—Pauly, Devries Smith & Deffner, L.L.C.

(57) ABSTRACT

The present invention relates to methods, devices, and coatings, wherein active agent release is determined by deposition rate of a coating or material. In an embodiment, the invention includes a method for coating a medical device, including identifying active agent elution rates for a coating composition applied to substrates at a plurality of coating deposition rates, selecting one of the coating deposition rates, and applying the coating composition to the medical device at the selected deposition rate. In an embodiment, the invention includes a combination including a medical device and a composition for coating the surface of a medical device with an active agent in a manner that permits the coated surface to release the active agent over time when implanted in vivo.

18 Claims, 4 Drawing Sheets

U.S. PATENT DOCUMENTS

| | | |
|---|---|---|
| 2003/0129130 A1 | 7/2003 | Guire et al. |
| 2003/0190420 A1 | 10/2003 | Chappa et al. |
| 2004/0062875 A1 | 4/2004 | Chappa et al. |
| 2004/0086569 A1 | 5/2004 | Sparer et al. |
| 2004/0089230 A1 | 5/2004 | Schwarz et al. |
| 2004/0194704 A1 | 10/2004 | Chappa et al. |
| 2005/0255142 A1 | 11/2005 | Chudzik et al. |
| 2007/0248637 A1* | 10/2007 | Chappa et al. .............. 424/422 |

FOREIGN PATENT DOCUMENTS

| | | |
|---|---|---|
| WO | WO 02/03890 A1 | 1/2002 |

* cited by examiner

METHODS, DEVICES, AND COATINGS FOR CONTROLLED ACTIVE AGENT RELEASE

This application claims the benefit of U.S. Provisional Application No. 60/608,638, filed Sep. 10, 2004, the contents of which is herein incorporated by reference.

FIELD OF THE INVENTION

The present invention relates to methods, devices, and coatings for controlled active agent release. More specifically, the present invention relates to methods, devices, and coatings, wherein active agent release rate is determined by deposition rate of a coating or material.

BACKGROUND OF THE INVENTION

Therapeutic benefits can be achieved in some instances by providing an active agent to a subject in a manner that extends the time over which the active agent is released. Further, therapeutic benefits can be achieved by providing an active agent to a specific target tissue, instead of systemically. This is because the effect of the agent on the target tissue can be maximized while limiting side effects on other tissues. One approach to providing these benefits is to use a coating system containing an active agent on a medical device.

The specific rate at which an active agent is eluted from a coating or material is of importance. If the active agent elutes too quickly, there may be too much of an active agent that is dosed to a particular tissue. Over-dosing of an active agent may have harmful side effects. If the active agent elutes too slowly, there may be too little of an active agent that is dosed to a particular tissue. Under-dosing of an active agent may fail to yield a therapeutic effect.

A desirable elution rate for one active agent may be different than a desirable elution rate for another active agent. Further, a desirable elution rate for a particular active agent may vary with the particular type of condition being treated.

Therefore, a need exists for coatings, coating systems, and coating methods that achieve a predetermined rate of elution of an active agent from a coating or material.

SUMMARY OF THE INVENTION

The present invention relates to methods, devices, and coatings, wherein active agent release is determined by deposition rate of a coating or material. In an embodiment, the invention includes a method for coating a medical device, including identifying active agent elution rates for a coating composition applied to substrates at a plurality of coating deposition rates, selecting one of the coating deposition rates, and applying the coating composition to the medical device at the selected deposition rate. In an embodiment, the invention includes a combination including a medical device and a composition for coating the surface of a medical device with an active agent in a manner that permits the coated surface to release the active agent over time when implanted in vivo.

The above summary of the present invention is not intended to describe each discussed embodiment of the present invention. This is the purpose of the figures and the detailed description that follows.

DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

Embodiments of the present invention can provide predetermined release rates of active agents. It has been surprisingly discovered that the release kinetics of an active agent from a coating or material can be predetermined by selecting the rate at which the coating or material is originally deposited onto a substrate. In some embodiments, depositing a coating material at a faster rate can result in a coating that has accelerated (or faster) active agent release kinetics. Conversely, in some embodiments, depositing a coating material at a slower rate can result in a coating that has decelerated (or slower) active agent release kinetics. In this manner, a preselected elution rate for an active agent can be achieved by adjusting the deposition rate of the coating material.

While not intending to be bound by theory, it is believed that deposition rate affects release kinetics at least partially because of the effects that solvents can have on the structure of the coating. Specifically, faster application is believed to allow more solvent to accumulate during the deposition process and result in a structural configuration of the coated composition that is distinct from the structural configuration that is produced by slower application of the coating material. In embodiments where the coating comprises multiple components, it is believed that faster application can allow a degree of separation of the components that can result in a structural configuration of the coated composition that impacts release kinetics. In some embodiments, faster application of the coating material can result in faster, or accelerated, release kinetics. In some embodiments, slower application of the coating material can result in slower, or decelerated, release kinetics.

The release kinetics of an active agent in vivo are thought to generally include both a short term ("burst") release component, within the order of minutes to hours or less after implantation, and a longer term release component, which can range from on the order of hours to days or even months of useful release. As used herein, the "acceleration" or "deceleration" of active agent release can include either or both of these release kinetics components. For example, in an embodiment, the invention includes accelerating or decelerating the release of an active agent over the first two hours after implantation. In an embodiment, the invention includes accelerating or decelerating the release of an active agent over the first 10 days after implantation. In an embodiment, the invention includes accelerating or decelerating the release of an active agent from between 10 and 40 days after implantation.

The term "coating composition", as used herein, will refer to one or more vehicles (e.g., a system of solutions, mixtures, emulsions, dispersions, blends, etc.) used to effectively coat a surface with an active agent and at least one polymer component, either individually or in any combination. A coating composition can be provided in any suitable form, e.g., in the form of a true solution, or fluid or paste-like emulsion, mixture, dispersion or blend. The term "coated composition" will refer to the combination, upon a surface, of active agent and at least one polymer component, whether formed as the result of one or more coating vehicles, or in one or more layers. The coated composition will generally result from the complete or partial removal of solvents or other volatile components and/or other physical-chemical actions (e.g, heating or illuminating) affecting the coated composition in situ upon the surface.

Figure 1:
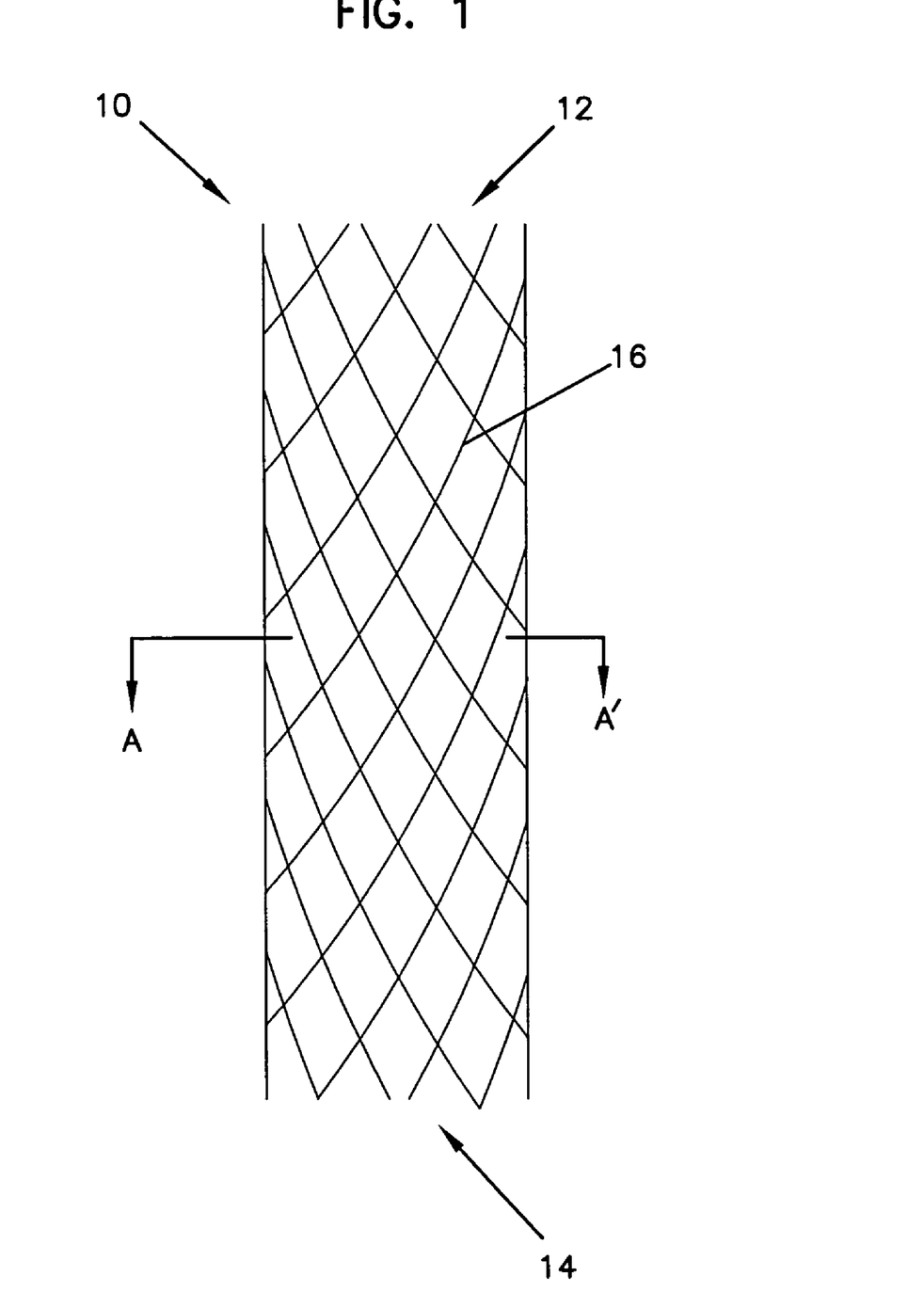
FIG. 1 an exemplary coated medical device in accordance with an embodiment of the invention.

Referring to FIG. 1, a view of an exemplary coated medical device 10 in accordance with an embodiment of the invention includes shown. In this case, the medical device is a stent. However, one of skill in the art will appreciate that many different kinds of devices can be coated in accordance with embodiments of the invention. Other exemplary devices are described below. The medical device has a first end 12 and a second end 14. In between the first end 12 and the second end 14 the device includes a plurality of stainless steel wires 16 (or threads). The stainless steel wires 16 are coated according to the methods of the invention.

Figure 2:
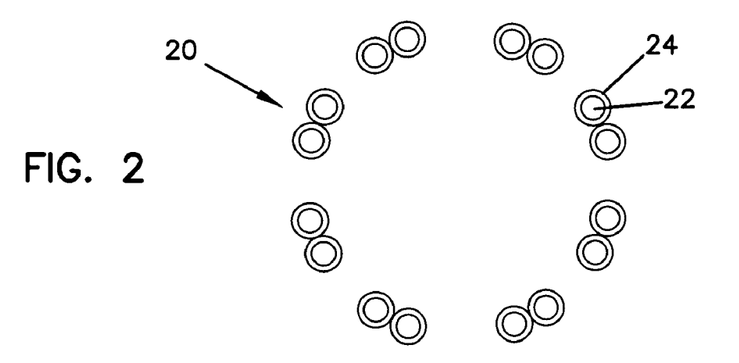
FIG. 2 is a cross-sectional view of the coated medical device of FIG. 1 taken along line A-A'.

Referring now to FIG. 2, a cross-sectional view 20 of the coated medical device of FIG. 1 taken along line A-A' is shown. In this view, the substrate 22 of the medical device 20 is shown, which in this case is stainless steel. One of skill in the art will appreciate that the substrate may comprise many different materials as described below. A coated composition 24, including an active agent and at least one polymer component, is disposed on the substrate 22.

Figure 3:
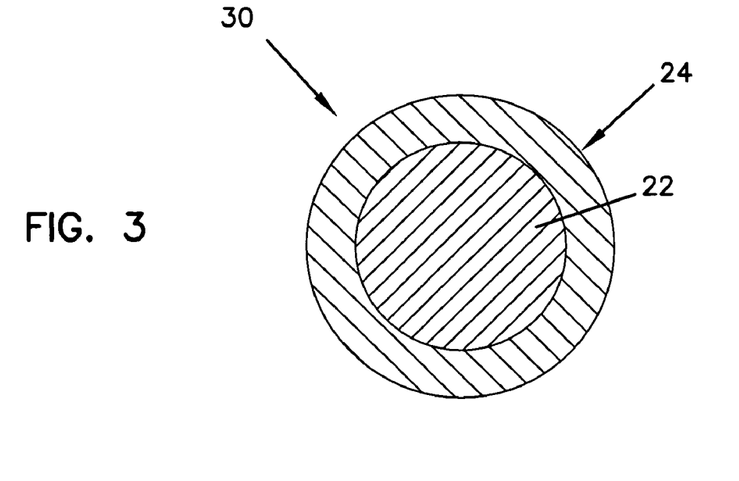
FIG. 3 is a cross-sectional view of a substrate with a coated composition in accordance with an embodiment of the invention.
Figure 4:
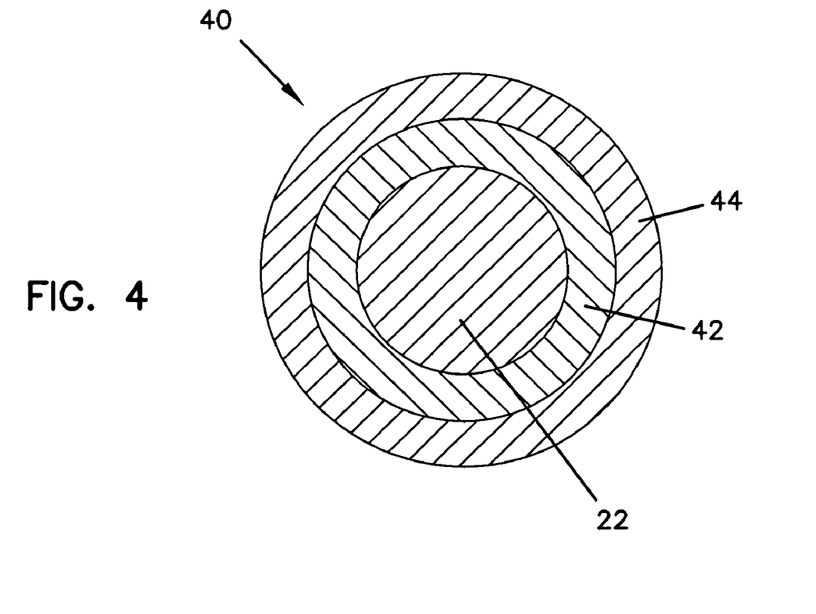
FIG. 4 is a cross-sectional view of a substrate with a multi-layered coating in accordance with another embodiment of the invention.

Referring now to FIG. 3, a cross-sectional view of a substrate coated with a coated composition is shown in accordance with an embodiment of the invention. The coated composition 24 surrounds the substrate 22. In other embodiments, there may be multiple layers of coatings surrounding the substrate. Referring now to FIG. 4, a cross-sectional view of a substrate with a multi-layered coating in accordance with another embodiment of the invention is shown. A first layer 42 surrounds the substrate 22. A second layer 44 surrounds the first layer 42. In an embodiment, first layer 42 is an active agent layer and second layer 44 comprises at least one polymer deposited in accordance with methods of the invention. Thus, embodiments of the present invention include multi-layered coatings wherein one or more of the layers is deposited in accordance with methods of the invention. One of skill in the art will appreciate that additional layers can also be deposited over, or under, those shown in FIG. 4, such that the coating can comprise more than two layers.

Embodiments of the invention also include devices, methods, and coatings where only one layer of a multi-layered coating is deposited at a predetermined application rate of the coating composition to achieve a selected elution rate of agent. Thus, in an embodiment, an active agent layer is deposited through methods known to those of skill in the art and then a layer including at least one polymer is deposited at a predetermined application rate of the coating composition to achieve a selected elution rate of agent. Similarly, in an embodiment, a vapor-deposited polymer (such as parylene) may be either underneath or on top of the layer containing at least one polymer that is deposited at a predetermined application rate to achieve a selected elution rate of agent. Various aspects of the invention will now be described in greater detail.

Coating Compositions:

Coating compositions can be prepared to include a solvent, at least one polymer component dissolved in the solvent, and an active agent or agents dispersed in the polymer/solvent mixture. However, in some embodiments, the coating composition contains only a solvent and at least one polymer and the active agent is provided separately. Examples of polymer solution solvents can include alcohols (e.g., methanol, butanol, propanol, and isopropanol), alkanes (e.g., halogenated such as chloroform or unhalogenated alkanes such as hexane and cyclohexane), amides (e.g., dimethylformamide), ethers (e.g., tetrahydrofuran (THF) and dioxolane), ketones (e.g., methylethylketone), aromatic compounds (e.g., toluene and xylene), nitrites (e.g., acetonitrile) and esters (e.g., ethyl acetate). In an embodiment, the coating composition contains mixtures of different solvents. In an embodiment, the solvent is one in which the one or more polymer components form a true solution. In an embodiment, the solvent is one or more of THF, chloroform, and methanol.

One of skill in the art will appreciate that different solvents may evaporate at different rates. Accordingly, the deposition rate that provides a particular active agent release rate may depend on the particular solvent being used.

Polymers

In an embodiment, the coating composition includes an active agent in combination with at least one polymer. In an embodiment, the coating composition includes an active agent in combination with a plurality of polymers, including a first polymer and a second polymer. In an embodiment, the coating composition includes an active agent in combination with a blend of polymers, including two or more polymers. When the coating composition contains only one polymer, it can be either a first or second polymer as described herein. As used herein, the term "(meth)acrylate" when used in describing polymers shall mean the form including the methyl group (methacrylate) or the form without the methyl group (acrylate). As used herein, the term "polymers" shall include co-polymers, unless indicated to the contrary.

Examples of suitable first polymers include poly(alkyl (meth)acrylates), and in particular, those with alkyl chain lengths from 2 to 8 carbons, and with molecular weights from 50 kilodaltons to 900 kilodaltons. An exemplary first polymer is poly(n-butyl methacrylate) (pBMA). Such polymers are available commercially, e.g., from Aldrich, with varying inherent viscosity, solubility, and form (e.g., as crystals or powder).

Examples of suitable first polymers also include polymers selected from the group consisting of poly(aryl(meth)acrylates), poly(aralkyl(meth)acrylates), and poly(aryloxyalkyl (meth)acrylates). Such terms are used to describe polymeric structures wherein at least one carbon chain and at least one aromatic ring are combined with acrylic groups, typically esters, to provide a composition of this invention. Exemplary polymeric structures include those with aryl groups having from 6 to 16 carbon atoms and with weight average molecular weights from about 50 kilodaltons to about 900 kilodaltons. Suitable poly(aralkyl (meth)acrylates), poly(arylalky(meth)acrylates) or poly(aryloxyalkyl(meth)acrylates) can be made from aromatic esters derived from alcohols also containing aromatic moieties. Examples of poly(aryl(meth)acrylates) include poly(9-anthracenyl methacrylate), poly(chlorophenyl acrylate), poly(methacryloxy-2-hydroxybenzophenone), poly(methacryloxybenzotriazole), poly(naphthyl acrylate) and -methacrylate), poly(4-nitrophenyl acrylate), poly(pentachloro(bromo, fluoro) acrylate) and -methacrylate), and poly(phenyl acrylate) and -methacrylate). Examples of poly(aralkyl(meth)acrylates) include poly(benzyl acrylate) and -methacrylate), poly(2-phenethyl acrylate) and -methacrylate, and poly(1-pyrenylmethyl methacrylate). Examples of poly(aryloxyalkyl(meth)acrylates) include poly(phenoxyethyl acrylate) and -methacrylate), and poly(polyethylene glycol phenyl ether acrylates) and -methacrylates with varying polyethylene glycol molecular weights.

Examples of suitable second polymers are available commercially and include poly(ethylene-co-vinyl acetate) (pEVA) having vinyl acetate concentrations of between about 10% and about 50% (12%, 14%, 18%, 25%, 33% versions are commercially available), in the form of beads, pellets, granules, etc. pEVA co-polymers with lower percent vinyl acetate become increasingly insoluble in typical solvents, whereas those with higher percent vinyl acetate become decreasingly durable.

An exemplary polymer mixture for use in this invention includes mixtures of pBMA and pEVA. This mixture of polymers can be useful with absolute polymer concentrations (i.e., the total combined concentrations of both polymers in the coating composition), of between about 0.25 and about 70 percent (wt). In some embodiments, individual polymer concentrations in the coating solution can be between about 0.05 and about 70 percent (wt). In an embodiment, the polymer mixture includes pBMA with a molecular weight of from 100 kilodaltons to 900 kilodaltons and a pEVA copolymer with a vinyl acetate content of from 24 to 36 weight percent. In an embodiment, the polymer mixture includes pBMA with a molecular weight of from 200 kilodaltons to 400 kilodaltons and a pEVA copolymer with a vinyl acetate content of from 30 to 34 weight percent. The concentration of the active agent or agents dissolved or suspended in the coating mixture can range from 0.01 to 90 percent, by weight, based on the weight of the final coating composition.

First polymers of the invention can also comprise one or more polymers selected from the group consisting of (i) poly(alkylene-co-alkyl(meth)acrylates, (ii) ethylene copolymers with other alkylenes, (iii) polybutenes, (iv) diolefin derived non-aromatic polymers and copolymers, (v) aromatic group-containing copolymers, and (vi) epichlorohydrin-containing polymers. Second polymers of the invention can also comprise a polymer selected from the group consisting of poly(alkyl(meth)acrylates) and poly(aromatic (meth)acrylates), where "(meth)" will be understood by those skilled in the art to include such molecules in either the acrylic and/or methacrylic form (corresponding to the acrylates and/or methacrylates, respectively).

Poly(alkylene-co-alkyl(meth)acrylates) include those copolymers in which the alkyl groups are either linear or branched, and substituted or unsubstituted with non-interfering groups or atoms. Such alkyl groups preferably comprise from 1 to 8 carbon atoms, inclusive, and more preferably, from 1 to 4 carbon atoms, inclusive. In an embodiment, the alkyl group is methyl. In some embodiments, copolymers that include such alkyl groups can comprise from about 15% to about 80% (wt) of alkyl acrylate. When the alkyl group is methyl, the polymer contains from about 20% to about 40% methyl acrylate in some embodiments, and from about 25 to about 30% methyl acrylate in a particular embodiment. When the alkyl group is ethyl, the polymer contains from about 15% to about 40% ethyl acrylate in an embodiment, and when the alkyl group is butyl, the polymer contains from about 20% to about 40% butyl acrylate in an embodiment.

Alternatively, first polymers for use in this invention can comprise ethylene copolymers with other alkylenes, which in turn, can include straight and branched alkylenes, as well as substituted or unsubstituted alkylenes. Examples include copolymers prepared from alkylenes that comprise from 3 to 8 branched or linear carbon atoms, inclusive. In an embodiment, copolymers prepared from alkylene groups that comprise from 3 to 4 branched or linear carbon atoms, inclusive. In a particular embodiment, copolymers prepared from alkylene groups containing 3 carbon atoms (e.g., propene). By way of example, the other alkylene is a straight chain alkylene (e.g., 1-alkylene). Exemplary copolymers of this type can comprise from about 20% to about 90% (based on moles) of ethylene. In an embodiment, copolymers of this type comprise from about 35% to about 80% (mole) of ethylene. Such copolymers will have a molecular weight of between about 30 kilodaltons to about 500 kilodaltons. Exemplary copolymers are selected from the group consisting of poly(ethylene-co-propylene), poly(ethylene-co-1-butene), polyethylene-co-1-butene-co-1-hexene) and/or poly(ethylene-co-1-octene).

"Polybutenes" suitable for use in the present invention includes polymers derived by homopolymerizing or randomly interpolymerizing isobutylene, 1-butene and/or 2-butene. The polybutene can be a homopolymer of any of the isomers or it can be a copolymer or a terpolymer of any of the monomers in any ratio. In an embodiment, the polybutene contains at least about 90% (wt) of isobutylene or 1-butene. In a particular embodiment, the polybutene contains at least about 90% (wt) of isobutylene. The polybutene may contain non-interfering amounts of other ingredients or additives, for instance it can contain up to 1000 ppm of an antioxidant (e.g., 2,6-di-tert-butyl-methylphenol butylated hydroxy toluene (BHT)). By way of example, the polybutene can have a molecular weight between about 150 kilodaltons and about 1,000 kilodaltons. In an embodiment, the polybutene can have between about 200 kilodaltons and about 600 kilodaltons. In a particular embodiment, the polybutene can have between about 350 kilodaltons and about 500 kilodaltons. Polybutenes having a molecular weight greater than about 600 kilodaltons, including greater than 1,000 kilodaltons are available but are expected to be more difficult to work with.

Additional alternative first polymers include diolefin-derived, non-aromatic polymers and copolymers, including those in which the diolefin monomer used to prepare the polymer or copolymer is selected from butadiene ($CH_2$=CH—CH=$CH_2$) and/or isoprene ($CH_2$=CH—C($CH_3$)=$CH_2$). In an embodiment, the polymer is a homopolymer derived from diolefin monomers or is a copolymer of diolefin monomer with non-aromatic mono-olefin monomer, and optionally, the homopolymer or copolymer can be partially hydrogenated. Such polymers can be selected from the group consisting of polybutadienes prepared by the polymerization of cis-, trans- and/or 1,2-monomer units, or from a mixture of all three monomers, and polyisoprenes prepared by the polymerization of cis-1,4- and/or trans-1,4-monomer units. Alternatively, the polymer is a copolymer, including graft copolymers, and random copolymers based on a non-aromatic mono-olefin monomer such as acrylonitrile, and an alkyl (meth)acrylate and/or isobutylene. In an embodiment, when the mono-olefin monomer is acrylonitrile, the interpolymerized acrylonitrile is present at up to about 50% by weight; and when the mono-olefin monomer is isobutylene, the diolefin is isoprene (e.g., to form what is commercially known as a "butyl rubber"). Exemplary polymers and copolymers have a Mw between about 150 kilodaltons and about 1,000 kilodaltons. In an embodiment, polymers and copolymers have a Mw between about 100 kilodaltons and about 200 kilodaltons with and without BHT.

Additional alternative first polymers include aromatic group-containing copolymers, including random copolymers, block copolymers and graft copolymers. In an embodiment, the aromatic group is incorporated into the copolymer via the polymerization of styrene. In a particular embodiment, the random copolymer is a copolymer derived from copolymerization of styrene monomer and one or more monomers selected from butadiene, isoprene, acrylonitrile, a $C_1$-$C_4$ alkyl (meth)acrylate (e.g., methyl methacrylate) and/or butene. Useful block copolymers include copolymer containing (a) blocks of polystyrene, (b) blocks of an polyolefin selected from polybutadiene, polyisoprene and/or polybutene (e.g., isobutylene), and (c) optionally a third monomer (e.g., ethylene) copolymerized in the polyolefin block. The aromatic group-containing copolymers contain about 10% to about 50% (wt) of polymerized aromatic monomer and the molecular weight of the copolymer is from about 300 kilodaltons to about 500 kilodaltons. In an embodiment, the molecular weight of the copolymer is from about 100 kilodaltons to about 300 kilodaltons.

Additional alternative first polymers include epichlorohydrin homopolymers and poly(epichlorohydrin-co-alkylene oxide) copolymers. In an embodiment, in the case of the copolymer, the copolymerized alkylene oxide is ethylene oxide. By way of example, epichlorohydrin content of the epichlorohydrin-containing polymer is from about 30% to 100% (wt). In an embodiment, epichlorohydrin content is from about 50% to 100% (wt). In an embodiment, the epichlorohydrin-containing polymers have an Mw from about 100 kilodaltons to about 300 kilodaltons.

Polymers can also include a poly(ether ester) multiblock copolymer based on poly(ethylene glycol) (PEG) and poly (butylene terephthalate) and can be described by the following general structure:

[—(OCH$_2$CH$_2$)$_n$—O—C(O)—C$_6$H$_4$—C(O)—]x[—
O—(CH$_2$)$_4$—O—C(O)—C$_6$H$_4$—C(O)—]y, where —C$_6$H$_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer. Preferably, n is selected such that the molecular weight of the PEG block is between about 300 and about 4000. Preferably, x and y are selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and active agent release characteristics (e.g., through controlled polymer degradation and swelling) by varying the values of n, x and y in the copolymer structure. Degradation of the copolymer does not create toxic degradation products or an acid environment, and its hydrophilic nature conserves the stability of labile active agents, such as proteins (e.g., lysozymes). Microspheres containing mixtures of block copolymers and active agents can easily be designed for use in situations requiring faster degradation.

In an embodiment, polymer systems of the present invention include microspheres based on dextran microspheres cross-linked through ester linkages. The microspheres are produced using a solvent-free process, thus avoiding the possibility of denaturing incorporated protein molecules. Loading levels as high as 15% (wt) protein can be achieved along with high encapsulation efficiencies (typically greater than 90%). Microsphere sizes of less than 50 um are possible, allowing for subcutaneous injection. The microsphere particles degrade through bulk erosion rather than surface erosion. No acidification occurs upon degradation, thus preserving the structural integrity of the protein molecules.

Polymers of the invention also include biodegradable polymers. Suitable biodegradable polymeric materials are selected from: (a) non-peptide polyamino polymers; (b) polyiminocarbonates; (c) amino acid-derived polycarbonates and polyarylates; and (d) poly(alkylene oxide) polymers. The biodegradable polymeric materials can break down to form degradation products that are non-toxic and do not cause a significant adverse reaction from the body.

In an embodiment, the biodegradable polymeric material is composed of a non-peptide polyamino acid polymer. Suitable non-peptide polyamino acid polymers are described, for example, in U.S. Pat. No. 4,638,045 ("Non-Peptide Polyamino Acid Bioerodible Polymers," Jan. 20, 1987). Generally speaking, these polymeric materials are derived from monomers, comprising two or three amino acid units having one of the following two structures illustrated below:

wherein the monomer units are joined via hydrolytically labile bonds at not less than one of the side groups $R_1$, $R_2$, and $R_3$, and where $R_1$, $R_2$, $R_3$ are the side chains of naturally occurring amino acids; Z is any desirable amine protecting group or hydrogen; and Y is any desirable carboxyl protecting group or hydroxyl. Each monomer unit comprises naturally occurring amino acids that are then polymerized as monomer units via linkages other than by the amide or "peptide" bond. The monomer units can be composed of two or three amino acids united through a peptide bond and thus comprise dipeptides or tripeptides. Regardless of the precise composition of the monomer unit, all are polymerized by hydrolytically labile bonds via their respective side chains rather than via the amino and carboxyl groups forming the amide bond typical of polypeptide chains. Such polymer compositions are non-toxic, are biodegradable, and can provide zero-order release kinetics for the delivery of active agents in a variety of therapeutic applications. According to these aspects, the amino acids are selected from naturally occurring L-alpha amino acids, including alanine, valine, leucine, isoleucine, proline, serine, threonine, aspartic acid, glutamic acid, asparagine, glutamine, lysine, hydroxylysine, arginine, hydroxyproline, methionine, cysteine, cystine, phenylalanine, tyrosine, tryptophan, histidine, citrulline, ornithine, lanthionine, hypoglycin A, β-alanine, γ-amino butyric acid, alpha aminoadipic acid, canavanine, venkolic acid, thiolhistidine, ergothionine, dihydroxyphenylalanine, and other amino acids well recognized and characterized in protein chemistry.

In an embodiment, the biodegradable polymeric material can be composed of polyiminocarbonates. Polyiminocarbonates are structurally related to polycarbonates, wherein imino groups (>C=NH) are present in the places normally occupied by carbonyl oxygen in the polycarbonates. Thus, the biodegradable component can be formed of polyiminocarbonates having linkages For example, one useful polyiminocarbonate has the general polymer structural formula wherein R is an organic divalent group containing a non-fused aromatic organic ring, and n is greater than 1. Embodiments of the R group within the general formula above are exemplified by, but is not limited to the following:

R group (a)

(b)

wherein R' is lower alkene $C_1$ to $C_6$

(c)

wherein n is an interger equal to or greater than 1, X is a hetero atom such as —O—, —S—, or a bridging group such as —NH—, —S(=O)—, —SO$_2$—, —C(=O)—, —C(CH$_3$)$_2$—, —CH(CH$_3$)—, —CH(CH$_3$)—CH$_2$—CH(CH$_3$)—, (d)

Also, compounds of the general formula can be utilized, wherein X is O, NH, or NR''', wherein R''' is a lower alkyl radical; and R'' is a divalent residue of a hydrocarbon including polymers such as a polyolefin, an oligoglycol or polyglycol such as polyalkylene glycol ether, a polyester, a polyurea, a polyamine, a polyurethane, or a polyamide. Exemplary starting material for use in accordance with these embodiments include diphenol compounds having the formula and dicyanate compounds having the formula with $R_1$ and $R_2$ being the same or different and being alkylene, arylene, alkylarylene or a functional group containing heteroatoms. $Z_1$, and $Z_2$ can each represent one or more of the same or different radicals selected from the group consisting of hydrogen, halogen, lower-alkyl, carboxyl, amino, nitro, thioether, sulfoxide, and sulfonyl. Preferably, each of $Z_1$ and $Z_2$ are hydrogen.

In an embodiment, the biodegradable polymeric material can be composed of various types of amino acid-derived polycarbonates and polyarylates. These amino acid-derived polycarbonates and polyarylates can be prepared by reacting certain amino acid-derived diphenol starting materials with either phosgene or dicarboxylic acids, respectively. Exemplary amino acid-derived diphenol starting materials for the preparation of the amino acid-derived polycarbonates and/or polyarylates of this embodiment are monomers that are capable of being polymerized to form polyiminocarbonates with glass transition temperatures ("Tg's") sufficiently low to permit thermal processing. The monomers according to this embodiment are diphenol compounds that are amino acid ester derivatives having the formula shown below:

in which $R_1$ is an alkyl group containing up to 18 carbon atoms.

In yet another embodiment, the biodegradable polymeric material can be composed of copolymers containing both hydrophilic poly(alkylene oxides) (PAO) and biodegradable sequences, wherein the hydrocarbon portion of each PAO unit contains from 1 to 4 carbon atoms, or 2 carbon atoms (i.e., the PAO is poly(ethylene oxide)). For example, useful biodegradable polymeric materials can be made of block copolymers containing PAO and amino acids or peptide sequences and contain one or more recurring structural units independently represented by the structure —L—$R_1$—L—$R_2$—, wherein $R_1$ is a poly(alkylene oxide), L is —O— or —NH—, and $R_2$ is an amino acid or peptide sequence containing two carboxylic acid groups and at least one pendent amino group. Other useful biodegradable polymeric materials are composed of polyarylate or polycarbonate random block copolymers that include tyrosine-derived diphenol monomers and poly(alkylene oxide), such as the polycarbonate shown below:

wherein $R_1$ is —CH=CH— or (—$CH_2$—)$_j$, in which j is 0 to 8; $R_2$ is selected from straight and branched alkyl and alkylaryl groups containing up to 18 carbon atoms and optionally containing at least one ether linkage, and derivatives of biologically and pharmaceutically active compounds covalently bonded to the copolymer; each $R_3$ is independently selected from alkylene groups containing 1 to 4 carbon atoms; y is between 5 and about 3000; and f is the percent molar fraction of alkylene oxide in the copolymer and ranges from about 0.01 to about 0.99.

In some embodiments, pendent carboxylic acid groups can be incorporated within the polymer bulk for polycarbonates, polyarylates, and/or poly(alkylene oxide) block copolymers thereof, to further control the rate of polymer backbone degradation and resorption.

Application of the Coating Composition:

The coating composition can be applied to a substrate or device using any suitable technique. By way of example, it can be applied directly to the surface of a device, or alternatively, to the surface of a surface-modified device, by spraying, or any conventional technique. In some embodiments, the composition may be deposited under conditions of controlled relative humidity. In an embodiment, the relative humidity is controlled at a level of between about 0% and about 95% relative humidity. In some embodiments, the relative humidity is controlled at a level of between about 20% and about 40% relative humidity. In an embodiment, the relative humidity is controlled at a level of about 30%.

The composition can be coated onto a device surface in one or more applications. The method of applying the coating composition to the device is typically governed by the geometry of the device and other process considerations. The coating is subsequently cured by complete or partial evaporation of the solvent. The curing process can be performed at room temperature, elevated temperature, or with the assistance of vacuum.

In an embodiment, the coating composition can be applied with any technique that allows the rate of deposition to be controlled. By way of example, the coating composition can be applied with spray coating machines using traditional nozzles or with spray coating machines containing nozzles with sonicating members. An exemplary sonicating nozzle can be described as having at least two independent members: a solution delivery member and an air delivery/sonicating member. The air delivery/sonicating member can include a channel bored though the body of the air delivery/sonicating member. Gas can be provided from a gas delivery line to an inlet on the air delivery/sonicating member and can travel through the channel to the tip where a stream of gas is generated. A coating solution is delivered through solution delivery member via a solution delivery line to the tip of the nozzle, where, at this point, the solution is sonicated at the tip of the air delivery/sonicating member, producing droplets of solution, and the droplets are drawn into and carried by the gas stream originating at the tip of the nozzle. An exemplary sonicating nozzle is the MicroFlux XL nozzle sold by SonoTek (Milton, N.Y.). Further coating equipment is described in U.S. Pat. No. 6,709,712 (Chappa et al.); U.S. Pat. No. 6,562,136 (Chappa et al.); U.S. Patent Application Publication 20030190420 (10/429,019, Chappa et al.); U.S. Patent Application Publication 20040194704 (Ser. No. 10/409,434, Chappa et al.); and U.S. Patent Application Publication 20040062875 (Ser. No. 10/256,349, Chappa et al.); and are all herein incorporated by reference.

While not limiting the present invention, it is believed that depositing a coating composition that contains polyalkyl (meth)acrylate and poly(ethylene-co-vinyl acetate) at an increased rate increases the opportunities for the two components to migrate and become less homogenous, forming regions of greater concentration of one of the components. It is further believed that depositing a coating composition that contains polyalkyl(meth)acrylate and polybutadiene at an increased rate increases the opportunities for the two components to migrate and become less homogenous, forming regions of greater concentration of one of the components. In an embodiment, the invention comprises a medical device with a coated composition including a polyalkyl(meth)acrylate and a poly(ethylene-co-vinyl acetate) disposed thereon having a structure that is characterized by regions of greater concentration of one of the components than the other. In an embodiment, the invention comprises a medical device with a coated composition including a polyalkyl(meth)acrylate and a polybutadiene disposed thereon having a structure that is characterized by regions of greater concentration of one of the components than the other.

Substrates

Embodiments of the invention provide the ability to deliver active agents from a variety of substrate surfaces including metals, polymers, ceramics, and natural materials.

Metals include, but are not limited to, titanium, stainless steel, and cobalt chromium. Suitable metals can also include the noble metals such as gold, silver, copper, and platinum. Finally, suitable metals can include alloys such as nitinol or cobalt chromium alloys.

Polymers include those formed of synthetic polymers, including oligomers, homopolymers, and copolymers resulting from either addition or condensation polymerizations. Examples include, but not limited to, acrylics such as those polymerized from methyl acrylate, methyl methacrylate, hydroxyethyl methacrylate, hydroxyethyl acrylate, acrylic acid, methacrylic acid, glyceryl acrylate, glyceryl methacrylate, methacrylamide, and acrylamide; vinyls such as ethylene, propylene, styrene, vinyl chloride, vinyl acetate, vinyl pyrrolidone, and vinylidene difluoride, condensation polymers including, but are not limited to, nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetheretherketone.

Embodiments of the invention can also include the use of ceramics as a substrate. The ceramics include, but are not limited to, silicon nitride, silicon carbide, zirconia, and alumina, as well as glass, silica, and sapphire.

Certain natural materials are also suitable including human tissue, when used as a component of a device, such as bone, cartilage, skin and teeth; and other organic materials such as wood, cellulose, compressed carbon, rubber, silk, wool, and cotton.

The composition of the substrate can also include resins, polysaccharides, silicon, or silica-based materials, glass, films, gels, and membranes.

Devices

Embodiments of the invention can be used with many different types of medical devices. These devices can include both implantable devices and non-implantable medical devices.

Embodiments of the invention can be used with implantable, or transitorily implantable, devices including, but not limited to, vascular devices such as grafts (e.g., abdominal aortic aneurysm grafts, etc.), stents (e.g., self-expanding stents typically made from nitinol, balloon-expanded stents typically prepared from stainless steel, degradable coronary stents, etc.), catheters (including arterial, intravenous, blood pressure, stent graft, etc.), valves (e.g., polymeric or carbon mechanical valves, tissue valves, valve designs including percutaneous, sewing cuff, and the like), embolic protection filters (including distal protection devices), vena cava filters, aneurysm exclusion devices, artificial hearts, cardiac jackets, and heart assist devices (including left ventricle assist devices), implantable defibrillators, electro-stimulation devices and leads (including pacemakers, lead adapters and lead connectors), implanted medical device power supplies (e.g., batteries, etc.), peripheral cardiovascular devices, atrial septal defect closures, left atrial appendage filters, valve annuloplasty devices (e.g., annuloplasty rings), mitral valve repair devices, vascular intervention devices, ventricular assist pumps, and vascular access devices (including parenteral feeding catheters, vascular access ports, central venous access catheters); surgical devices such as sutures of all types, staples, anastomosis devices (including anastomotic closures), suture anchors, hemostatic barriers, screws, plates, clips, vascular implants, tissue scaffolds, cerebro-spinal fluid shunts, shunts for hydrocephalus, drainage tubes, catheters including thoracic cavity suction drainage catheters, abscess drainage catheters, biliary drainage products, and implantable pumps; orthopedic devices such as joint implants, acetabular cups, patellar buttons, bone repair/augmentation devices, spinal devices (e.g., vertebral disks and the like), bone pins, cartilage repair devices, and artificial tendons; dental devices such as dental implants and dental fracture repair devices; drug delivery devices such as drug delivery pumps, implanted drug infusion tubes, drug infusion catheters, and intravitreal drug delivery devices; ophthalmic devices including orbital implants, glaucoma drain shunts and intraocular lenses; urological devices such as penile devices (e.g., impotence implants), sphincter, urethral, prostate, and bladder devices (e.g., incontinence devices, benign prostate hyperplasia management devices, prostate cancer implants, etc.), urinary catheters including indwelling ("Foley") and non-indwelling urinary catheters, and renal devices; synthetic prostheses such as breast prostheses and artificial organs (e.g., pancreas, liver, lungs, heart, etc.); respiratory devices including lung catheters; neurological devices such as neurostimulators, neurological catheters, neurovascular balloon catheters, neuro-aneurysm treatment coils, and neuropatches; ear nose and throat devices such as nasal buttons, nasal and airway splints, nasal tampons, ear wicks, ear drainage tubes, tympanostomy vent tubes, otological strips, laryngectomy tubes, esophageal tubes, esophageal stents, laryngeal stents, salivary bypass tubes, and tracheostomy tubes; biosensor devices including glucose sensors, cardiac sensors, intra-arterial blood gas sensors; oncological implants; and pain management implants.

Classes of suitable non-implantable devices can include dialysis devices and associated tubing, catheters, membranes, and grafts; autotransfusion devices; vascular and surgical devices including atherectomy catheters, angiographic catheters, intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, clot extraction catheters, percutaneous transluminal angioplasty catheters, electrophysiology catheters, breathing circuit connectors, stylets (vascular and non-vascular), coronary guide wires, peripheral guide wires; dialators (e.g., urinary, etc.); surgical instruments (e.g. scalpels and the like); endoscopic devices (such as endoscopic surgical tissue extractors, esophageal stethoscopes); and general medical and medically related devices including blood storage bags, umbilical tape, membranes, gloves, surgical drapes, wound dressings, wound management devices, needles, percutaneous closure devices, transducer protectors, pessary, uterine bleeding patches, PAP brushes, clamps (including bulldog clamps), cannulae, cell culture devices, materials for in vitro diagnostics, chromatographic support materials, infection control devices, colostomy bag attachment devices, birth control devices; disposable temperature probes; and pledgets.

Coatings of the invention can also be applied to devices other than medical devices. By way of example, coatings which elute agents that control the growth of biological organisms can be useful in a variety of contexts such as water delivery pipes, boat hulls, flumes, tanks, structures designed to be at least partially submerged, structures subject to biofilm formation, and the like.

Active Agents

As used herein, the term "active agent" means a compound that has a particular desired activity. For example, an active agent can be a therapeutic compound that exerts a specific activity on a subject. In some embodiments, active agent will, in turn, refer to a peptide, protein, carbohydrate, nucleic acid, lipid, polysaccharide or combinations thereof, or synthetic inorganic or organic molecule, that causes a desired biological effect when administered in vivo to an animal, including but not limited to birds and mammals, including humans. In some embodiments, the active agent can be a bioactive agent. Active agents can have many different types of elution profiles.

Active agents useful according to the invention include substances that possess desirable therapeutic characteristics for application to the implantation site. Active agents useful in the present invention can include many types of therapeutics including thrombin inhibitors, antithrombogenic agents, thrombolytic agents, fibrinolytic agents, anticoagulants, antiplatelet agents, vasospasm inhibitors, calcium channel blockers, steroids, vasodilators, anti-hypertensive agents, antimicrobial agents, antibiotics, antibacterial agents, antiparasite and/or antiprotozoal solutes, antiseptics, antifungals, angiogenic agents, anti-angiogenic agents, inhibitors of surface glycoprotein receptors, antimitotics, microtubule inhibitors, antisecretory agents, actin inhibitors, remodeling inhibitors, antisense nucleotides, anti-metabolites, miotic agents, antiproliferatives, anticancer chemotherapeutic agents, anti-neoplastic agents, antipolymerases, antivirals, anti-AIDS substances, anti-inflammatory steroids or non-steroidal anti-inflammatory agents, analgesics, antipyretics, immunosuppressive agents, immunomodulators, growth hormone antagonists, growth factors, radiotherapeutic agents, peptides, proteins, enzymes, extracellular matrix components, ACE inhibitors, free radical scavengers, chelators, antioxidants, photodynamic therapy agents, gene therapy agents, anesthetics, immunotoxins, neurotoxins, opioids, dopamine agonists, hypnotics, antihistamines, tranquilizers, anticonvulsants, muscle relaxants and anti-Parkinson substances, antispasmodics and muscle contractants, anticholinergics, ophthalmic agents, antiglaucoma solutes, prostaglandins, antidepressants, antipsychotic substances, neurotransmitters, anti-emetics, imaging agents, specific targeting agents, and cell response modifiers.

More specifically, in embodiments the active agent can include heparin, covalent heparin, synthetic heparin salts, or another thrombin inhibitor; hirudin, hirulog, argatroban, D-phenylalanyl-L-poly-L-arginyl chloromethyl ketone, or another antithrombogenic agent; urokinase, streptokinase, a tissue plasminogen activator, or another thrombolytic agent; a fibrinolytic agent; a vasospasm inhibitor; a calcium channel blocker, a nitrate, nitric oxide, a nitric oxide promoter, nitric oxide donors, dipyridamole, or another vasodilator; HYTRIN® or other antihypertensive agents; a glycoprotein IIb/IIIa inhibitor (abciximab) or another inhibitor of surface glycoprotein receptors; aspirin, ticlopidine, clopidogrel or another antiplatelet agent; colchicine or another antimitotic, or another microtubule inhibitor; dimethyl sulfoxide (DMSO), a retinoid, or another antisecretory agent; cytochalasin or another actin inhibitor; cell cycle inhibitors; remodeling inhibitors; deoxyribonucleic acid, an antisense nucleotide, or another agent for molecular genetic intervention; methotrexate, or another antimetabolite or antiproliferative agent; tamoxifen citrate, TAXOL® (paclitaxel), or the derivatives thereof, rapamycin (or other rapalogs), vinblastine, vincristine, vinorelbine, etoposide, tenopiside, dactinomycin (actinomycin D), daunorubicin, doxorubicin, idarubicin, anthracyclines, mitoxantrone, bleomycin, plicamycin (mithramycin), mitomycin, mechlorethamine, cyclophosphamide and its analogs, chlorambucil, ethylenimines, methylmelamines, alkyl sulfonates (e.g., busulfan), nitrosoureas (carmustine, etc.), streptozocin, methotrexate (used with many indications), fluorouracil, floxuridine, cytarabine, mercaptopurine, thioguanine, pentostatin, 2-chlorodeoxyadenosine, cisplatin, carboplatin, procarbazine, hydroxyurea, morpholino phosphorodiamidate oligomer or other anti-cancer chemotherapeutic agents; cyclosporin, tacrolimus (FK-506), pimecrolimus, azathioprine, mycophenolate mofetil, mTOR inhibitors, or another immunosuppressive agent; cortisol, cortisone, dexamethasone, dexamethasone sodium phosphate, dexamethasone acetate, dexamethasone derivatives, betamethasone, fludrocortisone, prednisone, prednisolone, 6U-methylprednisolone, triamcinolone (e.g., triamcinolone acetonide), or another steroidal agent; trapidil (a PDGF antagonist), angiopeptin (a growth hormone antagonist), angiogenin, a growth factor (such as vascular endothelial growth factor (VEGF)), or an anti-growth factor antibody (e.g., ranibizumab, which is sold under the tradename LUCENTIS®), or another growth factor antagonist or agonist; dopamine, bromocriptine mesylate, pergolide mesylate, or another dopamine agonist; 60Co (5.3 year half life), $^{192}$Ir (73.8 days), $^{32}$P (14.3 days), $^{111}$In (68 hours), $^{90}$Y (64 hours), $^{99}$Tc (6 hours), or another radiotherapeutic agent; iodine-containing compounds, barium-containing compounds, gold, tantalum, platinum, tungsten or another heavy metal functioning as a radiopaque agent; a peptide, a protein, an extracellular matrix component, a cellular component or another biologic agent; captopril, enalapril or another angiotensin converting enzyme (ACE) inhibitor; angiotensin receptor blockers; enzyme inhibitors (including growth factor signal transduction kinase inhibitors); ascorbic acid, alpha tocopherol, superoxide dismutase, deferoxamine, a 21-aminosteroid (lasaroid) or another free radical scavenger, iron chelator or antioxidant; a $^{14}$C-, $^{3}$H-, $^{131}$I-, $^{32}$P- or $^{36}$S-radiolabelled form or other radiolabelled form of any of the foregoing; an estrogen (such as estradiol, estriol, estrone, and the like) or another sex hormone; AZT or other antipolymerases; acyclovir, famciclovir, rimantadine hydrochloride, ganciclovir sodium, Norvir, Crixivan, or other antiviral agents; 5-aminolevulinic acid, meta-tetrahydroxyphenylchlorin, hexadecafluorozinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin, or other antibody targeted therapy agents; gene therapy agents; enalapril and other prodrugs; PROSCAR®, HYTRIN® or other agents for treating benign prostatic hyperplasia (BHP); mitotane, aminoglutethimide, breveldin, acetaminophen, etodalac, tolmetin, ketorolac, ibuprofen and derivatives, mefenamic acid, meclofenamic acid, piroxicam, tenoxicam, phenylbutazone, oxyphenbutazone, nabumetone, auranofin, aurothioglucose, gold sodium thiomalate, a mixture of any of these, or derivatives of any of these.

Other biologically useful compounds that can also be included in the active agent layer include, but are not limited to, hormones, β-blockers, anti-anginal agents, cardiac inotropic agents, corticosteroids, analgesics, anti-inflammatory agents, anti-arrhythmic agents, immunosuppressants, antibacterial agents, anti-hypertensive agents, anti-malarials, anti-neoplastic agents, anti-protozoal agents, anti-thyroid agents, sedatives, hypnotics and neuroleptics, diuretics, antiparkinsonian agents, gastro-intestinal agents, anti-viral agents, anti-diabetics, anti-epileptics, anti-fungal agents, histamine H-receptor antagonists, lipid regulating agents, muscle relaxants, nutritional agents such as vitamins and minerals, stimulants, nucleic acids, polypeptides, and vaccines.

Antibiotics are substances which inhibit the growth of or kill microorganisms. Antibiotics can be produced synthetically or by microorganisms. Examples of antibiotics include penicillin, tetracycline, chloramphenicol, minocycline, doxycycline, vancomycin, bacitracin, kanamycin, neomycin, gentamycin, erythromycin, geldanamycin, geldanamycin analogs, cephalosporins, or the like. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone.

Antiseptics are recognized as substances that prevent or arrest the growth or action of microorganisms, generally in a nonspecific fashion, e.g., either by inhibiting their activity or destroying them. Examples of antiseptics include silver sulfadiazine, chlorhexidine, glutaraldehyde, peracetic acid, sodium hypochlorite, phenols, phenolic compounds, iodophor compounds, quaternary ammonium compounds, and chlorine compounds.

Antiviral agents are substances capable of destroying or suppressing the replication of viruses. Examples of anti-viral agents include α-methyl-1-adamantanemethylamine, hydroxy-ethoxymethylguanine, adamantanamine, 5-iodo-2'-deoxyuridine, trifluorothymidine, interferon, and adenine arabinoside.

Enzyme inhibitors are substances that inhibit an enzymatic reaction. Examples of enzyme inhibitors include edrophonium chloride, N-methylphysostigmine, neostigmine bromide, physostigmine sulfate, tacrine HCL, tacrine, 1-hydroxy maleate, iodotubercidin, p-bromotetramisole, 10-(α-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylaminie, N-monomethyl-L-arginine acetate, carbidopa, 3-hydroxybenzylhydrazine HCl, hydralazine HCl, clorgyline HCl, deprenyl HCl L(−), deprenyl HCl D(+), hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-di-phenylvalerate hydrochloride, 3-isobutyl-1-methylxanthne, papaverine HCl, indomethacind, 2-cyclooctyl-2-hydroxyethylamine hydrochloride, 2,3-dichloro-α-methylbenzylamine (DCMB), 8,9-dichloro-2,3,4,5-tetrahydro-1H-2-benzazepine hydrochloride, p-aminoglutethimide, p-aminoglutethimide tartrate R(+), p-aminoglutethimide tartrate S(−), 3-iodotyrosine, alpha-methyltyrosine L(−), alpha-methyltyrosine D(−), cetazolamide, dichlorphenamide, 6-hydroxy-2-benzothiazolesulfonamide, and allopurinol.

Anti-pyretics are substances capable of relieving or reducing fever. Anti-inflammatory agents are substances capable of counteracting or suppressing inflammation. Examples of such agents include aspirin (salicylic acid), indomethacin, sodium indomethacin trihydrate, salicylamide, naproxen, colchicine, fenoprofen, sulindac, diflunisal, diclofenac, indoprofen and sodium salicylamide.

Local anesthetics are substances that have an anesthetic effect in a localized region. Examples of such anesthetics include procaine, lidocaine, tetracaine and dibucaine.

Imaging agents are agents capable of imaging a desired site, e.g., tumor, in vivo. Examples of imaging agents include substances having a label that is detectable in vivo, e.g., antibodies attached to fluorescent labels. The term antibody includes whole antibodies or fragments thereof.

Cell response modifiers are chemotactic factors such as platelet-derived growth factor (PDGF). Other chemotactic factors include neutrophil-activating protein, monocyte chemoattractant protein, macrophage-inflammatory protein, SIS (small inducible secreted), platelet factor, platelet basic protein, melanoma growth stimulating activity, epidermal growth factor, transforming growth factor alpha, fibroblast growth factor, platelet-derived endothelial cell growth factor, insulin-like growth factor, nerve growth factor, bone growth/cartilage-inducing factor (alpha and beta), and matrix metalloproteinase inhibitors. Other cell response modifiers are the interleukins, interleukin receptors, interleukin inhibitors, interferons, including alpha, beta, and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, activin, and DNA that encodes for the production of any of these proteins, antisense molecules, androgenic receptor blockers and statin agents.

The weight of the coating attributable to the active agent can be in any range desired for a given active agent in a given application. In some embodiments, weight of the coating attributable to the active agent is in the range of about 1 microgram to about 10 milligrams of active agent per $cm^2$ of the effective surface area of the device. By "effective" surface area it is meant the surface amenable to being coated with the composition itself. For a flat, nonporous, surface, for instance, this will generally be the macroscopic surface area itself, while for considerably more porous or convoluted (e.g., corrugated, pleated, or fibrous) surfaces the effective surface area can be significantly greater than the corresponding macroscopic surface area. In an embodiment, the weight of the coating attributable to the active agent is between about 0.01 mg and about 0.5 mg of active agent per $cm^2$ of the gross surface area of the device. In an embodiment, the weight of the coating attributable to the active agent is greater than about 0.01 mg.

In some embodiments, more than one active agent can be used as a part of the coated composition. Specifically, co-agents or co-drugs can be used. A co-agent or co-drug can act differently than the first agent or drug. The co-agent or co-drug can have an elution profile that is different than the first agent or drug. In an embodiment, the active agent can be in a microparticle.

In some embodiments, the active agent can be hydrophilic. In an embodiment, the active agent can have a molecular weight of less than 5 kilodaltons and can have a water solubility of greater than 10 mg/mL at 25 degrees Celsius. In some embodiments, the active agent can be hydrophobic. In an embodiment, the active agent can have a water solubility of less than 10 mg/mL at 25 degrees Celsius.

Further Embodiments of the Invention

In an embodiment, the invention includes a method for coating a medical device, including identifying active agent elution rates for a coating composition applied to substrates at a plurality of coating deposition rates, the coating composition comprising an active agent and a polymer, selecting one of the plurality of coating deposition rates with a desired active agent elution rate, and applying the coating composition to the medical device at the selected deposition rate. The coating composition can include a polyalkyl(meth)acrylate. The coating composition can include poly(n-butyl methacrylate). The coating composition can include at least two different polymers. The coating composition can include poly(ethylene-co-vinyl acetate) and poly(n-butyl methacrylate). The coating composition can include polybutadiene and poly(n-butyl methacrylate). In an embodiment, the total concentration of polymer in the coating composition is between about 0.25% and about 70% by weight, and the active agent is dissolved or suspended in the coating composition at a concentration of 0.01% to 90% by weight. The coating composition can include a solvent. The solvent can include one or more of an alcohol, an alkane, an amide, an ether, an ester, or an aromatic compound. The solvent can include one or more of THF, chloroform, or methanol. The medical device can be a stent. The active agent can include one or more of triamcinolone acetonide, dexamethasone, and TAXOL® (paclitaxel). The coating composition can be applied under a controlled level of relative humidity of between about 0% and about 95%.

In an embodiment, the invention includes a method of increasing the elution rate of an active agent from a coating composition, including increasing a deposition rate of the coating composition when applying the coating composition to a substrate, and achieving a predetermined increased elution rate. The coating composition can include at least two different polymers.

In an embodiment, the invention includes a method of decreasing the elution rate of an active agent from a coating composition, including decreasing a deposition rate of the coating composition when applying the coating composition to a substrate, and achieving a predetermined decreased elution rate. The coating composition can include at least two different polymers.

In an embodiment, the invention includes a combination including a medical device and a composition for coating the surface of a medical device with an active agent in a manner that permits the coated surface to release the active agent over time when implanted in vivo. The composition can include a bioactive agent in combination with at least one polymer. The medical device can be coated with the composition at a deposition rate that is pre-selected to provide a desired elution rate of the active agent. The coating composition can include at least two different polymers. The coating composition can include poly(ethylene-co-vinyl acetate) and poly(n-butyl methacrylate). The coating composition can include polybutadiene and poly(n-butyl methacrylate). In an embodiment, the total concentration of polymer in the coating composition is between about 0.25% and about 70% by weight, and the active agent is dissolved or suspended in the coating composition at a concentration of 0.01% to 90% by weight.

In an embodiment, the invention includes a method for coating a medical device, including applying an amount of a coating composition to a test substrate at a plurality of deposition rates, the coating composition including an active agent and at least one polymer. Then, determining an active agent release rate for at least one of the deposition rates and identifying a deposition rate that provides a desired active agent release rate. Finally, coating at least one medical device with the composition at the identified deposition rate.

In an embodiment, the invention includes a method for coating a medical device, including selecting a deposition rate for applying a coating composition including an active agent and a polymer, and applying the coating composition to the medical device at a deposition rate providing a predetermined elution rate.

In an embodiment, the invention includes a coated device including a substrate and a deposited coating including an active agent and having a pre-selected elution profile. In this embodiment, the elution profile is achieved by the deposition rate of the coating.

In an embodiment, the present invention includes a medical device including a structure configured for introduction into a subject, a composition including an active agent disposed on the structure, wherein the composition is deposited onto the structure at a pre-selected rate.

In an embodiment, the invention includes a method for coating a medical device, comprising selecting a deposition rate for applying a coating composition comprising an active agent and a polymer, and applying the coating composition to the medical device at a deposition rate providing a predetermined elution rate.

In an embodiment, the invention includes a method for producing coatings providing different elution rates of an active agent from the coating, the method comprising applying a composition at a first rate and a second rate; the lower rate of deposition providing the slower elution rate, wherein the coating composition comprises the active agent and a polymer.

Embodiments of the invention will now be described through the following examples. However, one of skill in the art will appreciate that these are only examples and do not serve to limit the scope of the invention.

Example 1

Modifying Predetermined Release of Triamcinolone Acetonide by Varying Deposition Rate A coating solution was prepared for deposition of an active agent, triamcinolone acetonide (TA) onto curved pieces of a metal alloy wire. TA was obtained from Pfizer Inc., (New York, N.Y.). The solution was comprised of 30 mg/ml TA, 6 mg/ml poly(ethylene-co-vinyl acetate) (PEVA) (MW 75 kD, 33% vinyl acetate), and 24 mg/ml poly(n-butyl methacrylate) (pBMA) (MW 250 kD) dissolved in tetrahydrofuran (THF). The solution was applied to two wire pieces (samples A and B) using an ultra sonic spray deposition method at a relative humidity of 10% and at a flow rate of 0.05 ml/minute. Then the solution was applied to another two wire pieces (sample C and D) using an ultra sonic spray deposition method at a relative humidity of 10% and at a flow rate of 0.08 ml/minute.

In vitro agent elution studies were completed to study the elution rate and recovery of TA from the coated pieces of wire. The pieces of wire were placed into vials containing a phosphate buffered saline (PBS) solution. At various time points over 23 hours, the vial solutions were analyzed for TA by measuring absorbance at 242 nm using a spectrophotometer. The absorbances were then plotted versus time. The absorbances are shown in Table 1 below. Absorbance readings directly correlate to drug amounts.

Figure 5:
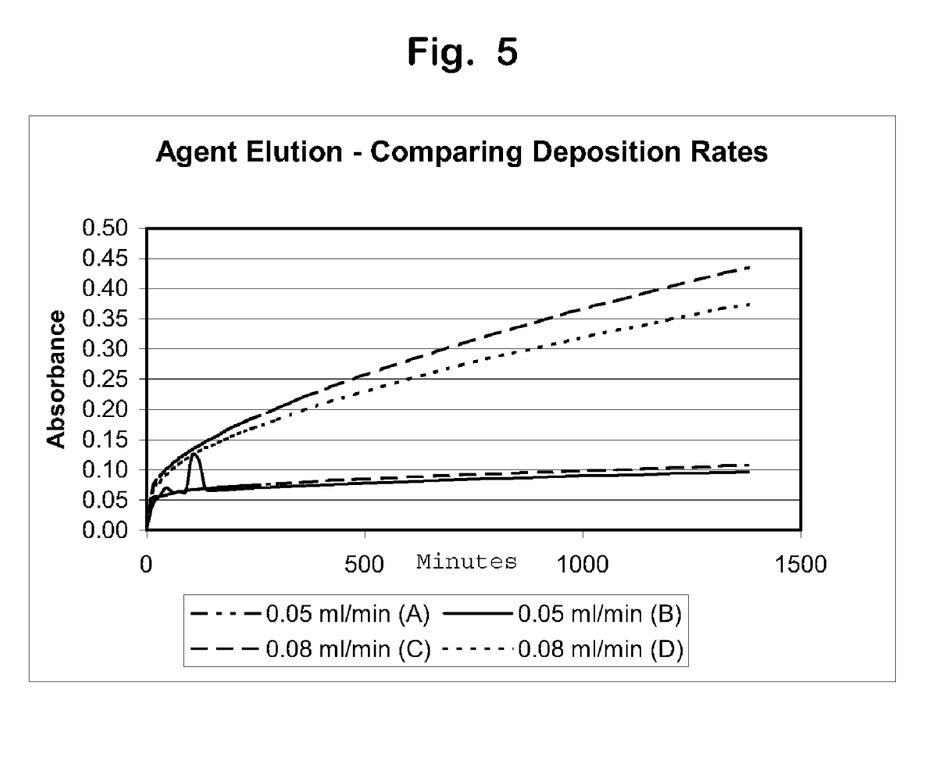
FIG. 5 is a graph showing the elution profile of triamcinolone acetonide from coatings deposited at a first rate compared with coatings deposited at a second rate.

The results are shown FIG. 5, wherein the lines reflect the experimental data. The results show that a composition deposited at a flow rate of 0.08 ml/min resulted in an agent elution rate that is signicantly faster than an identical composition that was deposited at a flow rate of 0.05 ml/min. The results show that, in some embodiments, the release kinetics of an active agent from a coating or material can be accelerated by increasing the rate with which the coating or material is deposited (or manipulating the flow rate) onto a substrate.

TABLE 1

| Time (minutes) | Sample A (0.05 ml/min) | Sample B (0.05 ml/min) | Sample C (0.08 ml/min) | Sample D (0.08 ml/min) |
| --- | --- | --- | --- | --- |
| 0 | 0.00000 | 0.00000 | 0.00000 | 0.00000 |
| 15 | 0.05205 | 0.04309 | 0.07128 | 0.06568 |
| 30 | 0.05566 | 0.05584 | 0.08873 | 0.07971 |
| 45 | 0.05825 | 0.07024 | 0.10001 | 0.09084 |
| 60 | 0.06125 | 0.06287 | 0.11027 | 0.10067 |
| 75 | 0.06385 | 0.06389 | 0.11890 | 0.10915 |
| 90 | 0.06485 | 0.06468 | 0.12606 | 0.11717 |
| 105 | 0.06722 | 0.12424 | 0.13338 | 0.12425 |
| 120 | 0.06769 | 0.11602 | 0.13979 | 0.13019 |
| 135 | 0.06932 | 0.06942 | 0.14625 | 0.13615 |

TABLE 1-continued

| Time (minutes) | Sample A (0.05 ml/min) | Sample B (0.05 ml/min) | Sample C (0.08 ml/min) | Sample D (0.08 ml/min) |
|---|---|---|---|---|
| 150 | 0.06992 | 0.06594 | 0.15186 | 0.14028 |
| 165 | 0.07065 | 0.06615 | 0.15694 | 0.14531 |
| 180 | 0.07138 | 0.06662 | 0.16442 | 0.15004 |
| 195 | 0.07236 | 0.06741 | 0.16988 | 0.15492 |
| 210 | 0.07293 | 0.06825 | 0.17482 | 0.15935 |
| 225 | 0.07403 | 0.06892 | 0.17968 | 0.16366 |
| 240 | 0.07454 | 0.06983 | 0.18452 | 0.16805 |
| 300 | 0.07672 | 0.07142 | 0.20178 | 0.18322 |
| 360 | 0.07949 | 0.07355 | 0.22083 | 0.19888 |
| 420 | 0.08215 | 0.07569 | 0.23718 | 0.21272 |
| 480 | 0.08427 | 0.07695 | 0.25251 | 0.22551 |
| 540 | 0.08602 | 0.07896 | 0.26693 | 0.23815 |
| 600 | 0.08812 | 0.08027 | 0.28100 | 0.25023 |
| 660 | 0.09023 | 0.08195 | 0.29459 | 0.26148 |
| 720 | 0.09216 | 0.08383 | 0.30839 | 0.27290 |
| 780 | 0.09345 | 0.08590 | 0.32127 | 0.28372 |
| 840 | 0.09447 | 0.08600 | 0.33383 | 0.29327 |
| 900 | 0.09599 | 0.08750 | 0.34598 | 0.30258 |
| 960 | 0.09792 | 0.08930 | 0.35873 | 0.31227 |
| 1020 | 0.09930 | 0.09046 | 0.37054 | 0.32261 |
| 1080 | 0.09978 | 0.09107 | 0.38071 | 0.33150 |
| 1140 | 0.10176 | 0.09196 | 0.39189 | 0.33916 |
| 1200 | 0.10333 | 0.09375 | 0.40327 | 0.34911 |
| 1260 | 0.10455 | 0.09429 | 0.41409 | 0.35800 |
| 1320 | 0.10660 | 0.09536 | 0.42525 | 0.36716 |
| 1380 | 0.10748 | 0.09629 | 0.43513 | 0.37327 |

Example 2

Modifying Predetermined Release of Triamcinolone Acetonide Over an Extended Period Time A coating solution was prepared for deposition of an active agent, triamcinolone acetonide (TA) onto curved pieces of metal alloy wire. TA was obtained from Pfizer Inc., (New York, N.Y.). The solution was comprised of 30 mg/ml TA, 6 mg/ml poly(ethylene-co-vinyl acetate) (PEVA) (MW 75 kD, 33% vinyl acetate), and 24 mg/ml poly(n-butyl methacrylate) (PBMA) (MW 250 kD) dissolved in THF. The solution was applied to one piece of wire (sample E) using an ultra sonic spray deposition method at a relative humidity of 10% and at a flow rate of 0.05 ml/minute, such that 972 µg of solids were deposited. Then the solution was applied to another piece of wire (sample F) using an ultra sonic spray deposition method at a relative humidity of 10% and at a flow rate of 0.08 ml/minute, such that 964 µg of solids were deposited.

In vitro agent elution studies were completed to study the elution rate and recovery of TA from the coated pieces of wire. The coated pieces of wire were placed into vials containing 4 ml of phosphate buffered saline (PBS). The PBS in each vial was stirred and the vials were kept in a water bath at a constant 37 degrees Celsius temperature. At various time points over 47 days, the coated pieces of wire were placed into new vials containing a fresh 4 ml of preheated PBS. The agent-containing 4 ml PBS samples were then analyzed for TA by measuring absorbance using a spectrophotometer. The absorbances were then converted into drug amounts using a standard curve. The drug amounts were then plotted versus time. The drug amounts are shown in Table 2 below.

Figure 6:
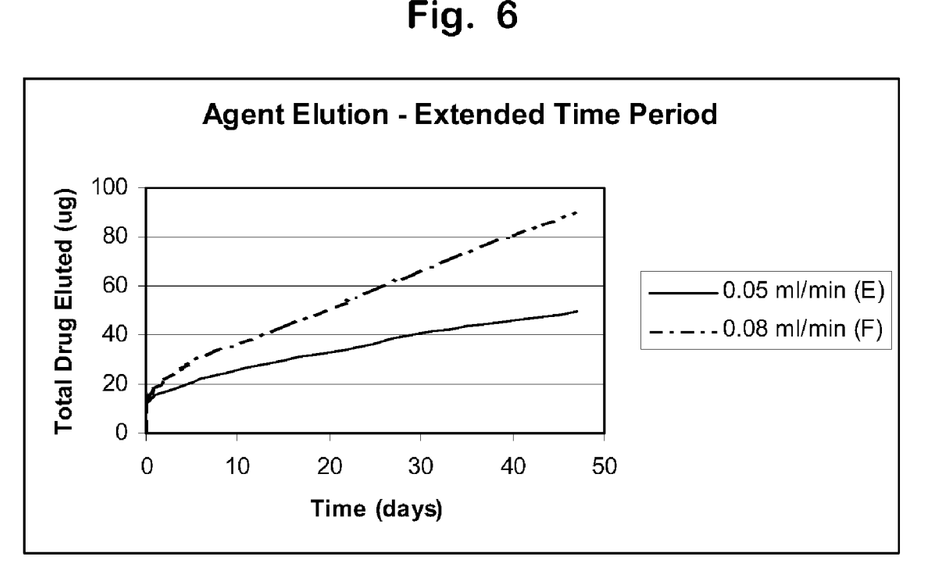
FIG. 6 is a graph showing the elution profile of triamcinolone acetonide a coating deposited at a first rate compared with a coating deposited at a second rate over an extended period of time.

The results are shown in FIG. 6, wherein the lines reflect the experimental data. The results show that a composition deposited at a flow rate of 0.08 ml/min resulted in an agent elution rate that is significantly faster than an identical composition that was deposited at a flow rate of 0.05 ml/min, and that this difference was maintained over 47 days. The results show that the release kinetics of an active agent from a coating or material can be determined over an extended period of time by manipulating the rate with which the coating or material is deposited (or manipulating the flow rate) onto a substrate.

TABLE 2

| Time | Sample E (0.05 ml/min) | Sample F (0.08 ml/min) |
|---|---|---|
| (hours) | | |
| 0 | 0 | 0 |
| 0.25 | 7.85 | 7.96 |
| 1 | 10.76 | 11.55 |
| 2 | 11.55 | 12.56 |
| 6.75 | 12.89 | 14.69 |
| (Days) | | |
| 1 | 15.25 | 18.39 |
| 2.1 | 17.27 | 21.87 |
| 3.9 | 19.62 | 27.02 |
| 7 | 22.65 | 32.74 |
| 15 | 29.38 | 43.95 |
| 20.9 | 33.53 | 51.8 |
| 24.9 | 36.55 | 58.42 |
| 29 | 39.81 | 64.81 |
| 33.1 | 42.5 | 71.09 |
| 37.2 | 44.52 | 77.03 |
| 40.1 | 45.86 | 80.96 |
| 43.3 | 47.65 | 85.44 |
| 47.1 | 49.56 | 90.6 |

Example 3

Modifying Predetermined Release of Dexamethasone by Varying Deposition Rate

A coating solution was prepared for deposition of an active agent, dexamethasone (Dex) onto metal coupons. Dex was obtained from Sigma-Aldrich (St. Louis Mo.). The solution was comprised of 10 mg/ml Dex, 10 mg/ml poly(ethylene-co-vinyl acetate) (pEVA) (MW 75 kD, 33% vinyl acetate), and 10 mg/ml poly(n-butyl methacrylate) (PBMA) (MW 250 kD) dissolved in a solvent of 80% vol. chloroform and 20% vol. methanol. The solution was applied to one side of six 8 mm×15 mm stainless steel (316 stainless steel) coupons (A-F) using an ultra sonic spray deposition method at a relative humidity of 30% and at varying flow rates as shown below in Table 3. Total solids deposited onto the coupons were as follows: A—1506 µg; B—1515 µg; C—1848 µg; D—1773 µg; E—1371 µg; F—1332 µg.

In vitro agent elution studies were completed to study the elution rate and recovery of Dex from the coated coupons. Elution was measured using a Sotax USP IV Flow-through Dissolution System. The elution set up was closed loop, therefore, the same medium volume is maintained throgh out the analysis. 36 ml of 2% SDS (sodium dodecyl sulfate) in water was used as the elution medium. The elution medium was kept at 37° C. Absorbance at 242 nm was measured using an Agilent 8453 UV spectrophotometer (with 8-cell multi-transport) at the time shown in Table 3 below. The absorbances were then plotted versus time. The absorbances are shown in Table 3 below. The absorbance readings were then converted into percentages of drug amounts eluted as shown in Table 4 below (it will be appreciated that amounts of drug eluted above 100% are within the experimental error for this technique of quantitating drug elution).

TABLE 3

(Absorbance)

| Time(hrs) | 0.04 ml/min | | 0.2 ml/min | | 1 ml/min | |
| --- | --- | --- | --- | --- | --- | --- |
| | A | B | C | D | E | F |
| 0.25 | 0.02238 | 0.02022 | 0.21608 | 0.20733 | 0.45093 | 0.4067 |
| 0.5 | 0.02872 | 0.02628 | 0.28752 | 0.27308 | 0.46606 | 0.43457 |
| 1 | 0.03692 | 0.03432 | 0.38879 | 0.37069 | 0.47131 | 0.44248 |
| 2 | 0.0463 | 0.04344 | 0.50015 | 0.47812 | 0.47484 | 0.44557 |
| 3 | 0.05388 | 0.05064 | 0.55499 | 0.53218 | 0.47686 | 0.45007 |
| 6 | 0.07047 | 0.0662 | 0.61078 | 0.58609 | 0.48111 | 0.45501 |
| 10 | 0.08628 | 0.08147 | 0.6283 | 0.60287 | 0.48338 | 0.4576 |
| 25 | 0.10991 | 0.10488 | 0.64518 | 0.62057 | 0.49732 | 0.46442 |
| 48 | 0.15741 | 0.14265 | 0.63911 | 0.6117 | 0.48216 | 0.45414 |
| 72 | 0.18073 | 0.19125 | 0.64016 | 0.61788 | 0.48596 | 0.4627 |
| 144 | 0.26904 | 0.29353 | 0.65336 | 0.63195 | 0.50106 | 0.46538 |

TABLE 4

(Percent Eluted)

| Time(hrs) | 0.04 ml/min | | 0.2 ml/min | | 1 ml/min | |
| --- | --- | --- | --- | --- | --- | --- |
| | A | B | C | D | E | F |
| 0.25 | 4.4 | 4.0 | 34.7 | 34.7 | 97.6 | 90.6 |
| 0.5 | 5.7 | 5.1 | 46.2 | 45.7 | 100.9 | 96.8 |
| 1 | 7.3 | 6.7 | 62.4 | 62.0 | 102.0 | 98.6 |
| 2 | 9.1 | 8.5 | 80.3 | 80.0 | 102.8 | 99.3 |
| 3 | 10.6 | 9.9 | 89.1 | 89.1 | 103.2 | 100.3 |
| 6 | 13.9 | 13.0 | 98.1 | 98.1 | 104.1 | 101.4 |
| 10 | 17.0 | 16.0 | 100.9 | 100.9 | 104.6 | 101.9 |
| 25 | 21.7 | 20.5 | 103.6 | 103.8 | 107.6 | 103.4 |
| 48 | 31.0 | 27.9 | 102.6 | 102.4 | 104.3 | 101.2 |
| 72 | 35.6 | 37.5 | 102.8 | 103.4 | 105.2 | 103.1 |
| 144 | 53.0 | 57.5 | 104.9 | 105.8 | 108.4 | 103.7 |

Figure 7:
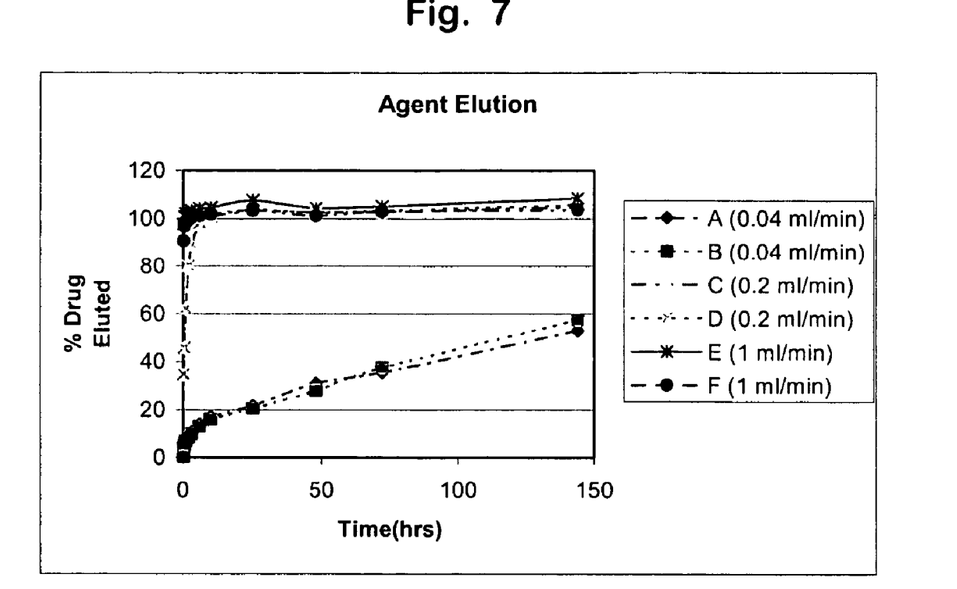
FIG. 7 is a graph showing the elution profile of dexamethasone from coatings applied at different rates.

The results are shown in FIG. 7, wherein the lines reflect the experimental data. The results show that a composition deposited at a flow rate of 0.04 ml/min resulted in an agent elution rate that is significantly slower than an identical composition that was deposited at a flow rate of 0.2 ml/min or at a flow rate of 1.0 ml/min. Therefore, the results further show that the release kinetics of an active agent from a coating or material can be manipulated by increasing or decreasing the rate with which the coating or material is deposited (or manipulating the flow rate) onto a substrate.

Example 5

Modifying Predetermined Release of Paclitaxel (TAXOL) by Varying Deposition Rate A coating solution was prepared for deposition of an active agent, paclitaxel (TAXOL®) onto metal coupons. Paclitaxel was obtained from LC Laboratories (Woburn, Mass.). The solution was comprised of 10 mg/ml paclitaxel, 10 mg/ml polybutadiene (PBD) (MW 160 kD), and 10 mg/ml poly(n-butyl methacrylate) (pBMA) (MW 250 kD), all dissolved in THF. The solution was applied to one side of six 8 mm×15 mm stainless steel (316 stainless steel) coupons using an ultra sonic spray deposition method at a relative humidity of 30% and at varying flow rates as shown below in Table 5. Total solids deposited onto the coupons were as follows: A-1398 µg; B-1377 µg; C-1404 µg; D-1386 µg; L-1578 µg; F-1560 µg.

In vitro agent elution studies were completed to study the elution rate and recovery of Dex from the coated coupons. Elution was measured using a Sotax USP IV Flow-through Dissolution System. The elution set up was closed loop, therefore, the same medium volume is maintained through out the analysis. 60 ml of 0.35% SDS (sodium dodecyl sulfate) in 0.0001 M acetate buffer was used as the elution medium. The elution medium was kept at 37° C. Absorbance at 231 nm was measured every 15 minutes for the first 3 hours, then every hour for 5 days using an Agilent 8453 UV spectrophotometer (with 8-cell multi-transport). The absorbances were then plotted versus time. The absorbances are shown in Table 5 below. Absorbance readings were then converted into drug amounts eluted as shown in Table 6 below.

TABLE 5

Absorbance

| Time(hrs) | 0.04 ml/min | | 0.2 ml/min | | 1 ml/min | |
| --- | --- | --- | --- | --- | --- | --- |
| | A | B | C | D | E | F |
| 0.25 | 0.0123 | 0.01234 | 0.01592 | 0.01442 | 0.08336 | 0.09246 |
| 0.5 | 0.01365 | 0.01351 | 0.01645 | 0.01466 | 0.10843 | 0.11322 |
| 2 | 0.0143 | 0.01413 | 0.01778 | 0.01514 | 0.15175 | 0.14896 |
| 6 | 0.01452 | 0.01452 | 0.01922 | 0.01544 | 0.16677 | 0.16219 |
| 24 | 0.01479 | 0.0154 | 0.02129 | 0.01607 | 0.18322 | 0.17463 |
| 48 | 0.01547 | 0.01647 | 0.02274 | 0.01638 | 0.19365 | 0.18266 |
| 72 | 0.0155 | 0.01687 | 0.02329 | 0.01618 | 0.20029 | 0.18796 |
| 96 | 0.01535 | 0.01723 | 0.02401 | 0.01617 | 0.20518 | 0.19222 |
| 120 | 0.01473 | 0.01654 | 0.02386 | 0.01556 | 0.208 | 0.1949 |

TABLE 6

Percent Eluted

| Time(hrs) | 0.04 ml/min | | 0.2 ml/min | | 1 ml/min | |
| --- | --- | --- | --- | --- | --- | --- |
| | A | B | C | D | E | F |
| 0.25 | 4.3 | 4.4 | 5.5 | 5.1 | 25.8 | 28.9 |
| 0.5 | 4.8 | 4.8 | 5.7 | 5.2 | 33.5 | 35.4 |
| 2 | 5.0 | 5.0 | 6.2 | 5.3 | 46.9 | 46.6 |
| 6 | 5.1 | 5.1 | 6.7 | 5.4 | 51.5 | 50.7 |
| 24 | 5.2 | 5.5 | 7.4 | 5.7 | 56.6 | 54.6 |
| 48 | 5.4 | 5.8 | 7.9 | 5.8 | 59.8 | 57.1 |
| 72 | 5.4 | 6.0 | 8.1 | 5.7 | 61.9 | 58.8 |
| 96 | 5.4 | 6.1 | 8.3 | 5.7 | 63.4 | 60.1 |
| 120 | 5.1 | 5.9 | 8.3 | 5.5 | 64.3 | 60.9 |

Figure 8:
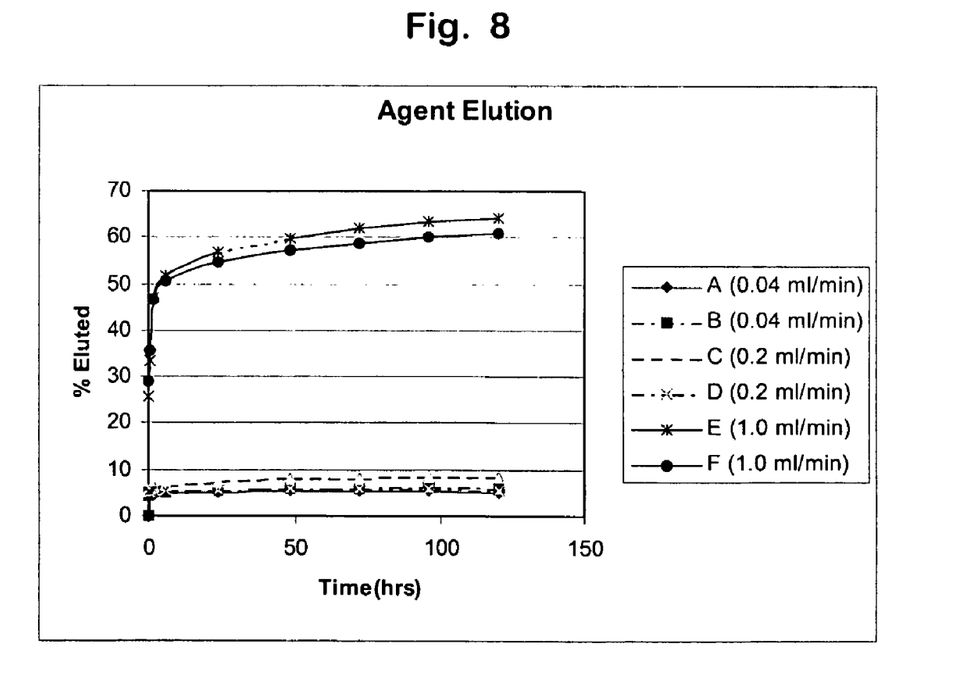
FIG. 8 is a graph showing the elution profile of paclitaxel (TAXOL) from coatings applied at different rates.

The results are shown in FIG. 8. The results show that a composition deposited at a flow rate of 1.0 ml/min resulted in an agent elution rate that is significantly faster than an identical composition that was deposited at a flow rate of 0.2 ml/min or at a flow rate of 0.04 ml/min. Therefore the results show that release kinetics of an active agent from a coating or material can be manipulated by increasing or decreasing the rate with which the coating or material is deposited (or manipulating the flow rate) onto a substrate.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

We claim:

1. A method for coating a medical device, comprising:
   identifying active agent elution rates for a coating composition applied to substrates at a plurality of coating deposition rates, the coating composition comprising an active agent and a polymer;
   selecting one of the plurality of coating deposition rates with a desired active agent elution rate, wherein the selected deposition rate is faster if a faster elution rate is desired and slower if a slower elution rate is desired, and
   applying the coating composition to the medical device at the selected deposition rate.

2. The method of claim 1, wherein the coating composition comprises a polyalkyl(meth)acrylate.

3. The method of claim 1, wherein the coating composition comprises poly(n-butyl methacrylate).

4. The method of claim 1, the coating composition comprising at least two different polymers.

5. The method of claim 4, wherein the coating composition comprises poly(ethylene-co-vinyl acetate) and poly(n-butyl methacrylate).

6. The method of claim 1, wherein the coating composition comprises polybutadiene and poly(n-butyl methacrylate).

7. The method of claim 1, wherein the total concentration of polymer in the coating composition is between about 0.25% and about 70% by weight, and the active agent is dissolved or suspended in the coating composition at a concentration of 0.01% to 90% by weight.

8. The method of claim 1, wherein the coating composition comprises a solvent.

9. The method of claim 8, wherein the solvent comprises one or more of an alcohol, an alkane, an amide, an ether, an ester, or an aromatic compound.

10. The method of claim 8, wherein the solvent is one or more of tetrahydrofuran, chloroform, or methanol.

11. The method of claim 1, wherein the medical device is a stent.

12. The method of claim 1, wherein the active agent comprises one or more of triamcinolone acetonide, dexamethasone, and paclitaxel.

13. The method of claim 1, wherein coating at least one medical device is conducted under a controlled level of relative humidity of between about 0% and about 95%.

14. The method of claim 1, wherein coating at least one medical device is conducted under a controlled level of relative humidity of between about 20% and about 40% relative humidity.

15. A method for coating a medical device comprising:
   applying an amount of a coating composition to a test substrate at a plurality of deposition rates, the coating composition including an active agent and at least one polymer;
   determining an active agent release rate for at least one of the deposition rates;
   identifying a deposition rate that provides a desired active agent release rate, wherein the identified deposition rate is faster if a faster elution rate is desired and slower if a slower elution rate is desired; and
   coating at least one medical device with the composition at the identified deposition rate.

16. The method of claim 15, the coating composition comprising at least two different polymers.

17. The method of claim 16, wherein the coating composition comprises poly(ethylene-co-vinyl acetate) and poly(n-butyl methacrylate).

18. The method of claim 16, wherein the coating composition comprises polybutadiene and poly(n-butyl methacrylate).

* * * * *